US008481261B2

(12) United States Patent
Lim et al.

(10) Patent No.: US 8,481,261 B2
(45) Date of Patent: Jul. 9, 2013

(54) NUCLEIC ACID EXTRACTION METHOD

(75) Inventors: Geun-Bae Lim, Pohang-si (KR); Ji-Min Kahng, Seoul (KR); Tae-Hee Kang, Incheon (KR); Jin-Hwa Jung, Pohang-si (KR)

(73) Assignees: Postech Academy-Industry Foundation, Pohang (KR); Catholic University Industry-Academic Cooperation Foundation, Seoul (KR)

( * ) Notice: Subject to any disclaimer, the term of this patent is extended or adjusted under 35 U.S.C. 154(b) by 0 days.

(21) Appl. No.: 13/001,444

(22) PCT Filed: Jun. 22, 2009

(86) PCT No.: PCT/KR2009/003341
§ 371 (c)(1),
(2), (4) Date: Aug. 17, 2011

(87) PCT Pub. No.: WO2009/157680
PCT Pub. Date: Dec. 30, 2009

(65) Prior Publication Data
US 2012/0088226 A1    Apr. 12, 2012

(30) Foreign Application Priority Data
Jun. 27, 2008    (KR) .................. 10-2008-0061903

(51) Int. Cl.
*C12Q 1/68* (2006.01)
*G01N 33/567* (2006.01)
*C12M 1/34* (2006.01)
*C07H 21/00* (2006.01)
*G01N 9/30* (2006.01)
*B01L 3/00* (2006.01)
*B01D 45/00* (2006.01)
*C12N 1/06* (2006.01)

(52) U.S. Cl.
USPC ......... 435/6.1; 435/7.2; 435/7.21; 435/283.1; 435/287.2; 435/259; 536/25.4; 422/72; 422/504; 422/533

(58) Field of Classification Search
USPC ............ 435/6.1, 7.2, 7.21, 259, 283.1, 287.2; 536/25.4; 422/72, 504, 533
See application file for complete search history.

(56) References Cited

U.S. PATENT DOCUMENTS 4,214,993 A    7/1980   Forsythe, Jr. et al.
4,750,982 A    6/1988   Tomblin et al.
(Continued)

FOREIGN PATENT DOCUMENTS

CN    1905806    1/2007
GB    2017911    10/1979
(Continued)

OTHER PUBLICATIONS

Miller et al, Evaluation of gel filtration resins for the removal of PCR-inhibitory substances from soils and sediments, 2001, Journal of Microbiological Methods, 44, 49-58.*
(Continued)

*Primary Examiner* — Narayan Bhat
(74) *Attorney, Agent, or Firm* — Lexyoume IP Meister, PLLC.

(57) ABSTRACT

The present invention relates to a nucleic acid extracting apparatus, and the nucleic acid extracting apparatus can include a pipe-shaped tube having an open outlet at one side thereof, and a hydrogel column that is provided inside the tube and filters impurities excluding an extraction target material.

19 Claims, 7 Drawing Sheets

U.S. PATENT DOCUMENTS

| | | | |
|---|---|---|---|
| 5,037,544 | A | 8/1991 | Snyder |
| 5,552,325 | A | 9/1996 | Nochumsom |
| 6,916,423 | B2 * | 7/2005 | Bogoev et al. ............ 210/634 |
| 2004/0072375 | A1 | 4/2004 | Gjerde et al. |

FOREIGN PATENT DOCUMENTS

| | | |
|---|---|---|
| JP | 2002-272462 | 9/2002 |
| KR | 10-1999-0082777 | 1/2001 |
| WO | 91/07648 | 5/1991 |
| WO | 2005/043117 | 5/2005 |
| WO | 2007/038523 | 4/2007 |

OTHER PUBLICATIONS

Bogner et al, Extraction of Nucleic Acids, 2006, Molecular Diagnostics: For the Clinical Laboratorian, Eds:Coleman and Tsongalis, Humana Press, pp. 25-30.*

Voytas, Resolution and Recovery of Large DNA Fragments, 2000, Current Protocols in Molecular Biology, Chapter 2, pp. 2.5A.1-2.5A.9.*

Sepharose Data Sheet, down loaded from the internet [www.gelifesciences.com] printed on Sep. 9, 2012, p. 1.*

Wang Z, Rossman TG. "Isolation of DNA fragments from agarose gel by centrifugation", Nucleic Acids Research, 1994, vol. 22, No. 14, pp. 2862-2863.

Jones, Clinton D et al., Core-shell microgel synthesis and the fundamentals of particle behavior, Abstract of Papers American Chemical Society, vol. 223, No. 1-2, 2002, page Coll 227.

Zhong, Luyang et al., Potential application of hydrogel-based strong anion-exchange membrane for plasmid DNA purification, Journal of Chromatography B, vol. 879, No. 9-10, Mar. 2011, pp. 564-572.

Chinese Patent Office, Search Report of the corresponding application (Chinese Patent Application No. 200980133927.X) (Feb. 17, 2013).

* cited by examiner

NUCLEIC ACID EXTRACTION METHOD

TECHNICAL FIELD

The present invention relates to a nucleic acid extracting apparatus, and more particularly, it relates to a nucleic acid extracting apparatus that uses a hydrogel column as a supporting member.

BACKGROUND ART

Recently, as causes of diseases has been explained at the gene level based on results of human genome studies, demand for modification and biochemical analysis of biological specimens for the purpose of cure and prevention of diseases has increased. In addition, a technique for extracting and analyzing nucleic acid from biological specimens or cell-included specimens is demanded not only for diagnosis of disease but also in various fields such as new drug discovery and development, pretesting for viral or bacteria infection, and forensic medicine.

When nucleic acid is extracted, low-purity nucleic acid suppresses or disturbs a hybridization reaction such as with Southern blotting and a chemical reaction such as an enzyme reaction, and nucleic acid contaminating material dissolves nucleic acid to be tested and causes an error in measurement of nucleic acid quantity. Such a contaminating material includes a low-molecular material such as fat, an enzyme inhibitor, an enzyme such as a protein, a polysaccharide, and a polynucleotide.

In order to maintain a high-purity nucleic acid for application to molecular biology, various methods have been developed for solving the above-stated problems.

A method for extracting nucleic acid from a cell includes a method in which a specimen including the cell is solubilized by being processed with sodium dodecyl sulfate (SDS) or proteinase K and then protein is denaturalized and eliminated with penyol so as to refine the nucleic acid. However, the phenol extraction method takes a long time since it includes many steps, and nucleic acid extraction efficiency greatly depends on skill of a worker.

Therefore, recently, a kit using a column has become a basic tool for nucleic acid extraction in order to reduce the above-stated problems. This tool uses a method with silica or fiberglass that uniquely combines with nucleic acid, and the method dissolves a cell by processing it with a chaotropic reagent and refines nucleic acid molecules from protein and other materials in the cell by using a structural interactive mechanism between a water molecule and nucleic acid.

The fiberglass or silica film has a low-combination ratio with a cell metabolic material, and therefore relatively highly-concentrated nucleic acid can be obtained. Although this method is more simple compared to the phenol extraction method, this method has drawbacks in complexity of operation and time consumption because the chaotropic reagent or ethanol that strongly blocks an enzyme reaction such as PCR should be completely eliminated.

Recently, a method for directly refining nucleic acid by using a filter has been disclosed in the Internal Publication No. WO 00/21973. In this method, a cell is attached to a filter by passing a specimen through the filter, the attached cell is dissolved and filtered through the filter, and then nucleic acid attached to the filter is washed and eluted. However, in order to elute nucleic acid after attaching the cell to the filter, the filter should be selected in accordance with a cell type.

The above information disclosed in this Background section is only for enhancement of understanding of the background of the invention and therefore it may contain information that does not form the prior art that is already known in this country to a person of ordinary skill in the art.

DETAILED DESCRIPTION

Technical Problem

To solve the above problems, the present invention has been made in an effort to provide an extracting apparatus that can more stably and easily extract nucleic acid.

Technical Solution

A nucleic acid extracting method according to an exemplary embodiment of the present invention may include forming a hydrogel column inside a pipe-shaped tube, forming a cell lysate by breaking cells, filtering nucleic acid for emitting the nucleic acid through the hydrogel column, and externally extracting the nucleic acid passed through the hydrogel column.

The hydrogel column may be formed of an agarose gel, and the agarose gel may include 1% to 2% agarose.

In addition, the forming of the hydrogel column may further include dissolving agarose by adding the agarose into distilled water and heating the mixture, and the forming of the hydrogel column may further include injecting the mixture of the distilled water and the agarose into a tube and hardening the mixture.

The nucleic acid extracting method may further include forming an injection groove that is extended in the length direction of the tube in the hydrogel column, and the injection groove may be formed in the center of the hydrogel column. In addition, the nucleic acid extracting method may further include forming a plurality of pressure reducing holes that contact the hydrogel column at an external circumference of the tube.

The forming of the cell lysate may include adding a lysis buffer and a proteinase K into a cell, and the forming of the cell lysate may further include adding an RNase into a cell. In addition, the hydrogel column may be formed in a rotating body shape.

The filtering of the nucleic acid may filter nucleic acid by using a centrifugal separation method, and the centrifugal separation method may include rotating the hydrogel column with a speed range of 1000 rpm to 3000 rpm. The filtering of the nucleic acid may be performed by using electricity or pressure. The cell may be a biological sample, and may be formed of one selected from a group of an animal sample, a plant sample, and a microscopic organism sample.

The nucleic acid may be formed of DNA. In addition, the nucleic acid extracting method according to the present invention may include using extracted nucleic acid in a genome test or a DNA chip test. In addition, the nucleic acid extracting method according to the present invention may include using extracted nucleic acid in point-of-care testing.

In addition, the nucleic acid extracting method may be applied to nucleic acid extraction for testing a human-derived cell that includes blood, blood serum, blood plasma, bone marrow, urine, feces, sputum, cell aspirate, tissue, and a tissue-derived material.

Advantageous Effects

According to the exemplary embodiment of the present invention, nucleic acid can be easily extracted without impurities by using a hydrogel supporting member as a filter.

In addition, pure nucleic acid can be obtained by using agarose gel as the hydrogel supporting member.

Nucleic acid recovery efficiency can be improved by forming an injection groove in the hydrogel supporting member.

Further, nucleic acid can be more easily extracted while reducing damage to the nucleic acid by forming a pressure-reducing hole in a tube.

Figure 1:
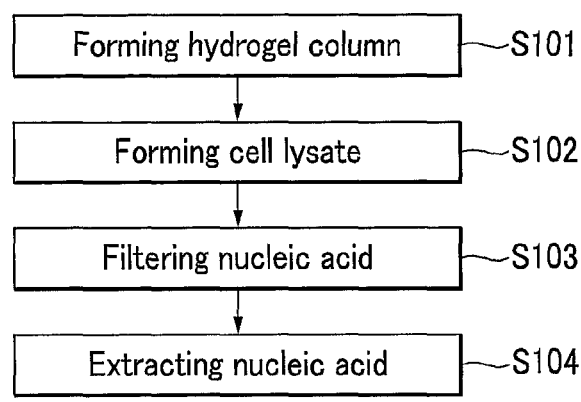
FIG. 1 is a flowchart of a nucleic acid extracting method according to a first exemplary embodiment of the present invention.

<Description of Reference Numerals Indicating Primary Elements in the Drawings>

| 12: housing | 13: cover |
|---|---|
| 14: tube | 15: pressure reducing hole |
| 16: hydrogel column | 18: injection groove |

BEST MODE

The present invention will be described more fully hereinafter with reference to the accompanying drawings, in which exemplary embodiments of the invention are shown. As those skilled in the art would realize, the described embodiments may be modified in various different ways, all without departing from the spirit or scope of the present invention. The drawings and description are to be regarded as illustrative in nature and not restrictive. Like reference numerals designate like elements throughout the specification.

Figure 2:
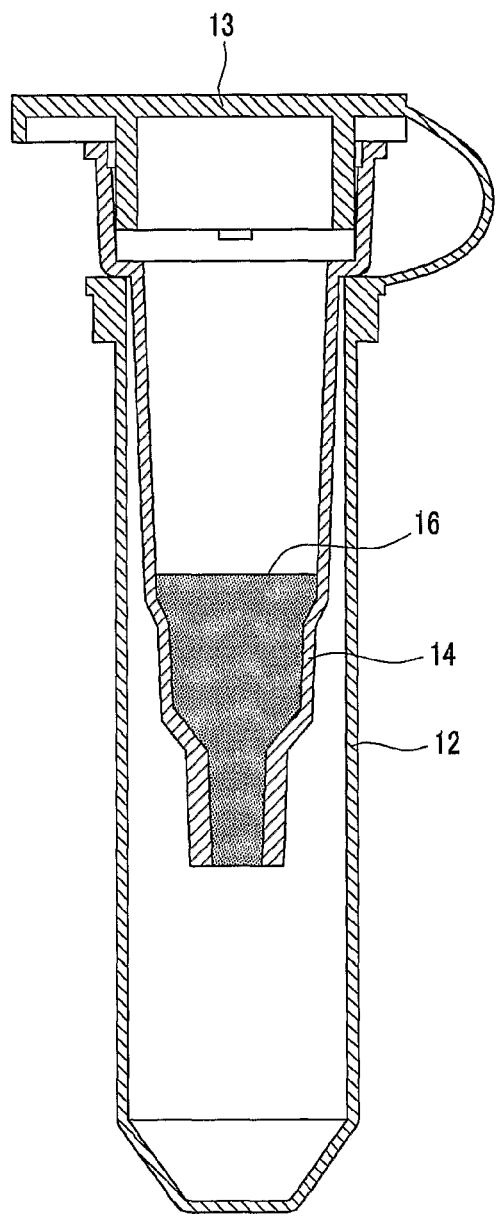
FIG. 2 is a cross-sectional view of a nucleic acid extracting apparatus according to the first exemplary embodiment of the present invention.
Figure 3:
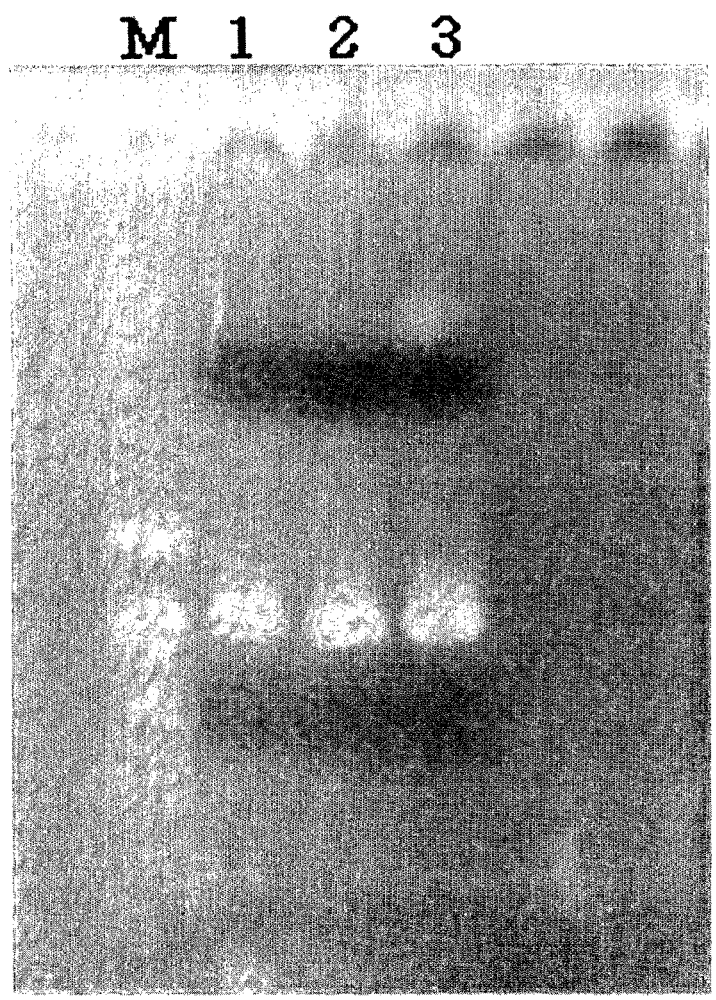
FIG. 3 is an electrophoresis photo of genomic DNA of an MC3T3 osteoblast separated by using the nucleic acid extracting apparatus according to the present invention.

FIG. 1 is a flowchart of a nucleic acid extracting method according to a first exemplary embodiment of the present invention, and FIG. 2 is a cross-sectional view of the nucleic acid extracting method according to the first exemplary embodiment of the present invention. Referring to FIG. 1 and FIG. 2, the nucleic acid extracting method according to the first exemplary embodiment of the present invention includes forming a hydrogel column 16 (S101), forming cell lysate (S102), filtering nucleic acid (S103), and extracting nucleic acid (S104).

First, in the forming of the hydrogel column 16 (S101), the hydrogel column 16 is formed in a pipe-shaped tube 14 that is provided inside a nucleic acid extracting apparatus. The hydrogel column 16 is formed inside the nucleic acid extracting apparatus, and the nucleic acid extracting apparatus includes a housing 12 that forms an external shape thereof, a tube 14 that is inserted into the housing 12, the tube 14, and a cover 12 that covers the tube 14.

The housing 12 is formed of a cylindrical pipe having a space therein, and a lower portion thereof is closed. In addition, the interior diameter of the housing 12 is gradually decreased toward the bottom thereof so that extracted nucleic acid or acid can be collected therein.

The tube 14 is inserted inside the housing, and a space is formed therein for containing cell lysate. An outlet 24 that is open bottomward is formed in a lower portion of the tube 14 so that nucleic acid can move to the housing therethrough. The interior diameter of the outlet 24 is smaller than other portions thereof for passing only nucleic acid excluding proteins and the like therethrough.

The hydrogel column 16 is provided in the tube 14, and has a shape that corresponds to the internal shape of the tube 14. Here, the shape is approximately columnar, and has a rotating body.

The hydrogel supporting member 16 in the present exemplary embodiment is formed of agarose gel that can be easily formed and is harmless to the human body. However, the present exemplary embodiment is not limited thereof, and various hydrogels can be applied.

In further detail of the forming of the hydrogel column 16, agarose is added into distilled water and then the agarose is dissolved by heating the mixture so as to make an agarose aqueous solution. Then, the agarose aqueous solution is injected into the tube 14 and the tube 14 is left at room temperature so as to form the column-shaped hydrogel supporting member 16.

The hydrogel supporting member 16 includes agarose in a concentration of 1.0% to 2.0%, and the volume thereof may be 300 μl to 600 μl.

In application of a centrifugal separating method, when the concentration of the agarose is lower than 1.0% in the hydrogel column 16, the hydrogel column 16 can be easily broken during the centrifugal separation process, and when the concentration of the agarose is higher than 2.0%, an aperture becomes too small to sufficiently extract the nucleic acid.

The hydrogel is a polymer material that can contains moisture, and has a three-dimensional network structure in which molecules are connected to each other by chemical and physical combinations. In addition, the hydrogel contains moisture by a hydrophilic functional group, capillary action, and osmotic pressure. Accordingly, the hydrogel has superior air permeability and percolate absorption, and is friendly to blood, body fluids, and body tissue.

Next, the forming of the cell lysate (S102) will be described. The cell lysate refers to a mixture that includes cell components obtained by destroying the cell.

The cell may be formed of a biological sample of an animal, a plant, or a microscopic organism.

The cell lysate can be made by adding a lysis buffer into a container in which a cell is contained, and the lysis buffer may be formed of various commercially available materials. In addition, a proteinase K which is a protein hydrolase or an RNase which is a ribo DNAase may be further included in addition to the lysis buffer.

In the present exemplary embodiment, lysis buffer at 180 μl, and proteinase K at 20 μl are added to a nucleic acid specimen, and the mixture is left at 55° C. for 20 minutes in order to break cells. After that, RNase at 20 μl is further added and the mixture is left at room temperature for two more minutes to form cell lysate.

The filtering of nucleic acid (S103) will now be described in further detail.

The cell lysate is inserted into the tube 14 where the hydrogel column 16 is formed and then a centrifugal separation process is performed. In this case, the centrifugal separation process includes rotation that is performed three times, each time taking 5 minutes, at 2000 rpm/200 rcf in a micro-centrifugal separator.

The rotation in the centrifugal separation process is performed at a low-speed in order to prevent the hydrogel column 16 from being damaged, and the rotation speed may be in a range of 1000 rpm to 3000 rpm. When the rotation speed is lower than 1000 rpm, the centrifugal separation process cannot be properly performed so that nucleic acid cannot pass through the hydrogel column 16, and when the rotation speed is higher than 3000 rpm, the hydrogel column 16 is damaged.

During the centrifugal separation process, nucleic acid is passed through the hydrogel column 16 and emitted to the housing 12 through the outlet 24, and foreign materials such as proteins that cannot pass through the hydrogel remain behind.

In the present exemplary embodiment, DNA is extracted by using the centrifugal separator, but the present invention is not limited thereto. Therefore, the nucleic acid can be extracted by using pressure or an electrical method, and in this case, the hydrogel column 16 is used as a filter.

When pressure or an electrical method is used, the hydrogel column 16 can include agarose at 0.5% to 5.0%. When extracting nucleic acid by using pressure, it is desirable that the hydrogel column 16 includes the agarose at less than 5.0% in order to prevent the hydrogel column 16 from being easily broken. When the agarose is included at more than 5.0%, the pore size thereof is reduced so that the nucleic acid cannot pass through the hydrogel column 16.

In addition, when the electrical method is used, it is advantageous when the size of the pores is relatively large, and therefore it is desirable to include 0.5% or more agarose. When the hydrogel column 16 includes less than 0.5% agarose, the size of the pores becomes too large, and the hydrogel column 16 may by broken due to pressure or a foreign material may be separated through the agarose gel column.

The hydrogel column 16 is hydrophilic and has a three-dimensional network structure, and therefore it can function as a nucleic acid filter during the centrifugal separation process. That is, since the nucleic acid included in the cell extract is small in size and is hydrophilic, it may pass through the pores formed in the hydrogel column 16 and be emitted through the outlet 24. However, a relatively large and non-aqueous phase liquid impurity such as a protein cannot pass through the hydrogel supporting member 16 so that it remains in the tube 14.

In the extracting of the nucleic acid, the nucleic acid having passed through the hydrogel column 16 is emitted out through the outlet 24 of the tube 14 and moves to the bottom of the housing 12.

The extracted nucleic acid may be used in a genome test or a DNA chip test. Therefore, the nucleic acid extracting method according to the present exemplary embodiment may include using extracted acid in a genome test or using the extracted acid in a DNA chip test.

In addition, the extracted nucleic acid may be applied in a point-of-care test (generally referred to as a POC test). Therefore, the nucleic acid extracting method according to the present exemplary embodiment may further include using the extracted nucleic acid in a POC test.

The POC test is a test that can be performed to diagnose a disease of a patient at a clinic or hospital setting or at the home of a patient. The nucleic acid extracting apparatus according to the present exemplary embodiment can extract nucleic acid with a simple structure, and therefore the extracted nucleic acid can be easily applied to the POC test.

In addition, the nucleic acid extracting method according to the present exemplary embodiment may be applied to nucleic acid extraction for testing a human-derived specimen that includes blood, blood serum, blood plasma, bone marrow, urine, feces, sputum, cell aspirate, tissue, and a tissue-derived material.

FIG. 2 shows an electrophoresis result of nucleic acid stored in the bottom of the housing 12.

FIG. 2 is an electrophoresis photo of genomic DNA of an MC3T3 osteoblast separated by using the nucleic acid extracting apparatus according to the first exemplary embodiment of the present invention. In FIG. 2, lane M is a standard DNA marker, and lane 1 and lane 2 are electrophoresis results of the genomic DNA of the MC3T3 osteoblast obtained by using a method according to the present invention.

Figure 4:
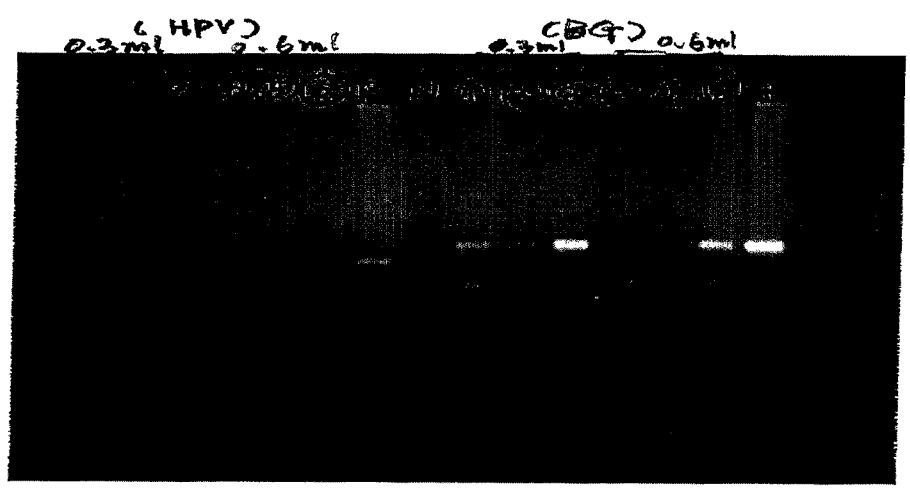
FIG. 4 is a photo of a polymerase chain reaction result for checking purity of the genomic DNA of the MC3T3 osteoblast separated by using the nucleic acid extracting method according to the first exemplary embodiment of the present invention.

FIG. 4 is a photo of a polymerase chain reaction result for checking purity of the genomic DNA of the MC3T3 osteoblast separated by using the nucleic acid extracting apparatus according to the first exemplary embodiment of the present invention.

In FIG. 4, lane M is a standard DNA marker, and lane 1 is an electrophoresis result after amplifying glyceraldehyde-3-phosphate dehydrogenase (G3PHD) in the genomic DNA of the MC3T3 osteoblast obtained by using the method according to the present invention. Lanes 2 and 3 are electrophoresis results after amplifying G3PHD in genomic DNA of the MC3T3 osteoblast obtained by using a commercially available genomic DNA extracting apparatus.

In the present exemplary embodiment, DNA is applied as the nucleic acid, but the present invention is not limited thereto. That is, the present exemplary embodiment can be applied to nucleic acid separation of various kinds, such as RNA.

An experiment for measuring a DNA extraction possibility and a proper gel concentration level from clinical specimens by using an agarose gel supporting member was performed.

In order to exclude an influence of a PCR reaction inhibitor, a test that included a hybridization process was selected from among tests using DNA.

One among cervical swab specimens on which a human papilloma virus (HPV) DNA chip test was selected and DNA extraction was performed on the selected specimen by using a nucleic acid extracting apparatus with an agarose gel column, and an HPV DNA chip test was performed on a result of the DNA extraction. In order to estimate sensitivity, an electrophoresis reading was performed after a general PCR test. The specimen was HPV-58, and Proteinase K at 20 μl, a specimen for HPV test at 400 μl, and a lysis buffer at 200 μl were added into a tube where the agarose gel column was present, and then centrifugal separation was performed three times for 5 minutes each time at 2000 rpm/200 rcf. As the agarose gel column, a column having a volume of 0.3 ml and a column having a volume of 0.6 ml were used.

When reading a result of the general PCR test with electrophoresis, results of both the 0.3 ml and 0.6 ml columns could be read only at a 2% agarose gel concentration. Meanwhile, in the DNA chip test in which a result can be obtained even if the number of DNA copies is low, an accurate HPV type result could be obtained in an agarose gel concentration of 1%, 1.5%, and 2% in the 0.3 ml column and in an agarose gel concentration of 2% in the 0.6 ml column.

According to the results of the present experiment, the general PCR test and the DNA chip test for obtaining HPV type information could be performed on both the 0.3 ml and 0.6 ml columns when agarose gel of 2% was used.

The following Table 1 shows experiment conditions of each lane.

|  | 0.3 ml | | | 0.6 ml | | |
| --- | --- | --- | --- | --- | --- | --- |
| Specimen No. | 1 | 2 | 3 | 4 | 5 | 6 |
| Agarose concentration | 1.0% | 1.5% | 2.0% | 1.0% | 1.5% | 2.0% |
| Agarose pore size | 150 nm | 500 nm |  | 150 nm | 500 nm |  |
| Electrophoresis result | − | − | + | − | − | + |
| HPV DNA Chip | Pos 58 | Pos 58 | Pos 58 | Fail | Fail | Pos 58 |

Figure 5:
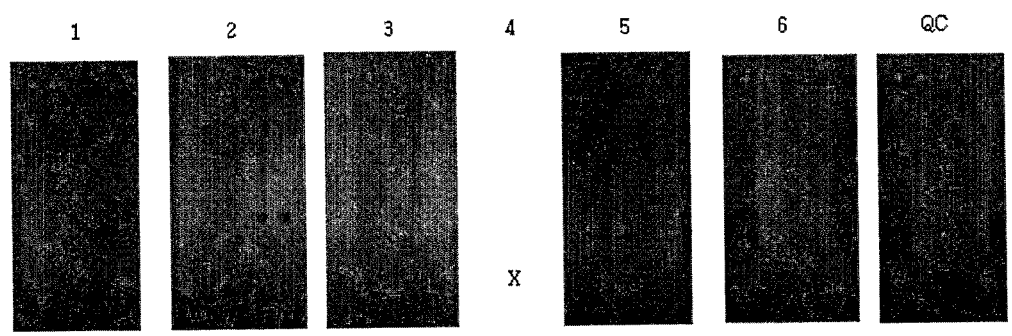
FIG. 5 is a photo of an electrophoresis result after PCR of nucleic acid of an HPV cell extracted by using the nucleic acid extracting method according to the first exemplary embodiment of the present invention.
Figure 6:
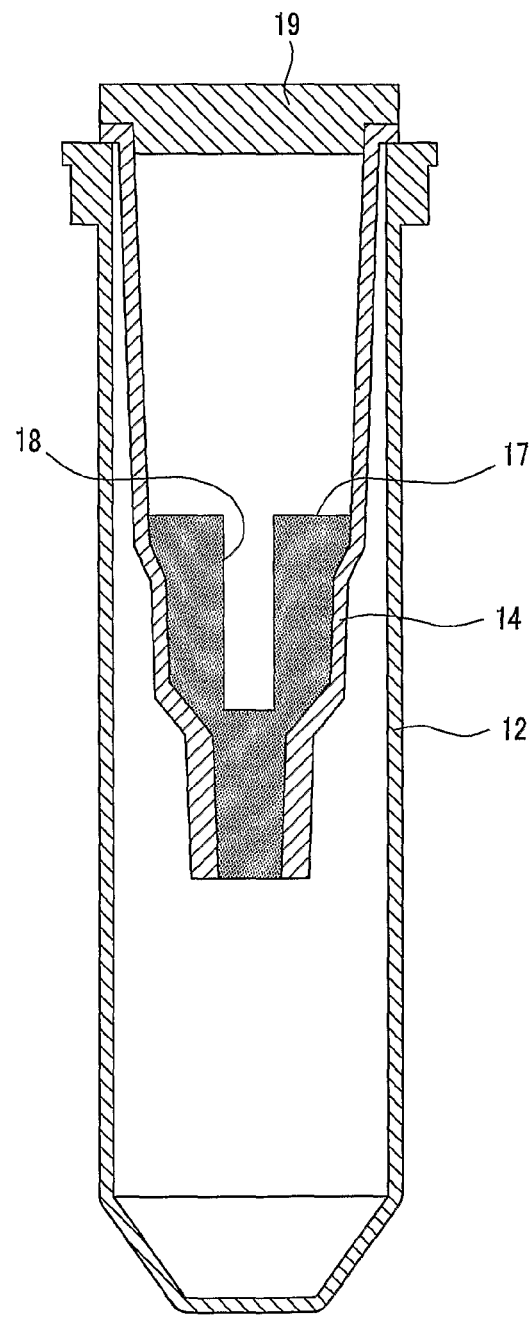
FIG. 6 is a photo of a nucleic acid chip test result of nucleic acid of the HPV cell extracted by using the nucleic acid extracting apparatus according to the first exemplary embodiment of the present invention.

FIG. 5 is a photo showing an electrophoresis result after PCR of HPV cell DNA extracted by using the nucleic acid extracting method according to the first exemplary embodiment of the present invention, and FIG. 6 is a photo of a nucleic acid chip test result of the HPV cell nucleic acid extracted by using the nucleic acid extracting method according to the first exemplary embodiment of the present invention.

As shown in FIG. 5 and FIG. 6, when a result of a general PCR test is read with electrophoresis, the result could be read only when both of the 0.3 ml and 0.6 ml columns are in an agarose gel of 2%. Meanwhile, in the DNA chip test in which a result can be obtained even though the number of DNA copies is low, an accurate HPV type result could be obtained in agarose gel of 1%, 1.5%, and 2% in the 0.3 ml column and in agarose gel of 2% in the 0.6 ml column.

According to the results of the experiment, the general PCR test and the DNA chip test for obtaining HPV type information could be performed on both the 0.3 ml and 0.6 ml columns when agarose gel of 2% was used.

An experiment was performed to compare the nucleic acid extracting apparatus according to the present exemplary embodiment with a nucleic acid extracting method that has been commonly used so as to evaluate the nucleic acid extraction efficiency of the nucleic acid extracting apparatus of the present exemplary embodiment.

For nucleic acid extraction of a clinical specimen stored in the nucleic acid extracted state, nucleic acid was extracted by using a commonly used nucleic acid extracting apparatus and the nucleic acid extracting apparatus according to the present exemplary embodiment, and then a recovery ratios of each method were compared by measuring concentrations of the extracted nucleic acid.

HPV-18 was used as a specimen, and proteinase K at 20 μl, DNA extraction specimen at 200 μl, and lysis buffer at 200 μl were added to the specimen, and centrifugal separation was performed on the mixture at 2000 rpm/200 rcf for 15 minutes. In the experiment, the agarose gel at a concentration of 2.0% and the hydrogel columns respectively having 0.3 ml and 0.6 ml volumes were used. With reference to DNA-acid concentration of 65 μg/ml of DNA extract used in the test, the commonly-used nucleic acid extracting method provides 14 μg/ml, that is, approximately a 21.5% recovery rate, and 2% agarose gel 0.3 ml and 0.6 ml respectively provided 19 μg/ml and 10 μg/ml, that is, approximately 29.2% and 15.4% recovery rates. Therefore, the result of the comparison demonstrates that the efficiency of the nucleic acid extracting apparatus of the present exemplary embodiment is included within a range for clinical application. As described, the nucleic acid extracting apparatus of the present exemplary embodiment is particularly advantageous to extract DNA of a biological specimen.

Figure 7:
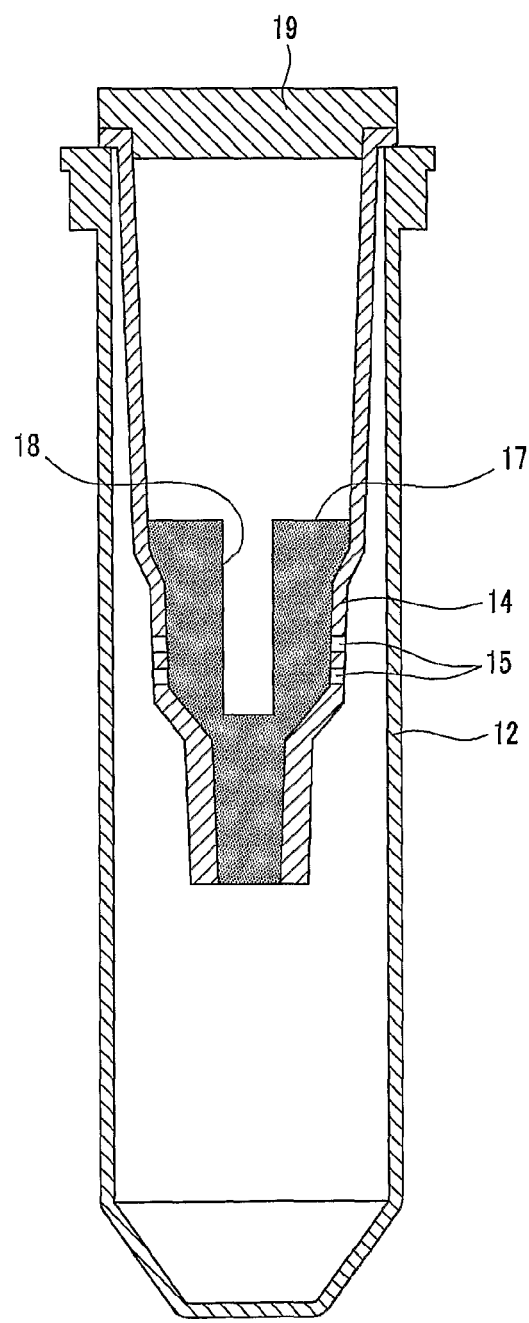
FIG. 7 is a cross-sectional view of a nucleic acid extracting apparatus according to a second exemplary embodiment of the present invention.

FIG. 7 is a cross-sectional view of a nucleic acid extracting apparatus used in a nucleic acid extracting method according to a second exemplary embodiment of the present invention.

Referring to FIG. 7, a nucleic acid extracting apparatus according to the present exemplary embodiment includes a cylindrical housing 12, a tube 14 inserted inside the housing 12, a hydrogel column 17 provided in the tube 14, and a cover 19 that covers the tube 14.

The nucleic acid extracting method according to the present exemplary embodiment further includes forming an injection groove 18 inside the hydrogel column 17. The injection groove 18 is positioned in a center of the hydrogel column 17, and may be formed in a cylindrical shape. Such an injection groove 18 can contain cell lysate, and reduces a distance between an outlet 24 and the cell lysate, thereby improving nucleic acid recovery efficiency. A plurality of micropores are formed in the hydrogel column 17, and nucleic acid is emitted to the outlet 24 through the plurality of micropores during the centrifugal separation process. Accordingly, when the distance between the cell lysate and the outlet 24 is decreased, the nucleic acid can more easily pass through the hydrogel column 17 so that the nucleic acid recovery efficiency can be improved.

Figure 8:
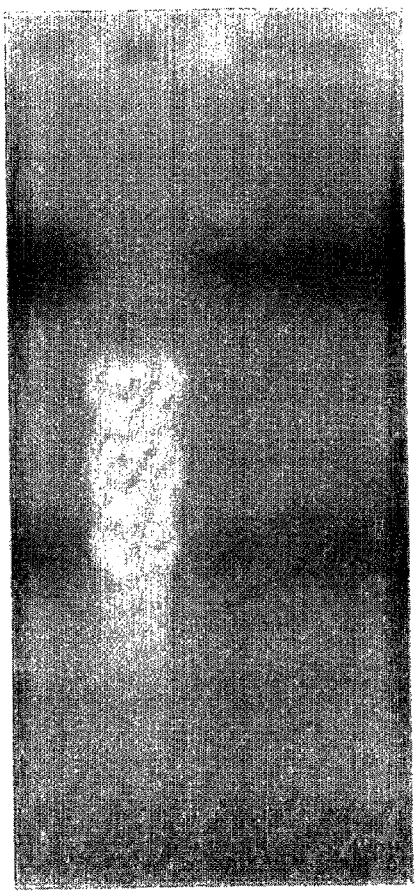
FIG. 8 is a cross-sectional view of a nucleic acid extracting apparatus used in a nucleic acid extracting method according to a third exemplary embodiment of the present invention.

FIG. 8 is a cross-sectional view of a nucleic acid extracting apparatus used in a nucleic acid extracting method according to a third exemplary embodiment of the present invention.

Referring to FIG. 8, a nucleic acid extracting apparatus according to the present exemplary embodiment includes a cylindrical housing 12, a tube 14 inserted into the housing 12, a hydrogel column 17 installed inside the tube 14, and a cover 19 that covers the tube 14.

In addition, the nucleic acid extracting method according to the present exemplary embodiment includes forming a pressure reducing hole 15 at an external circumference of the tube 14 where the hydrogel column 17 is formed.

A plurality of pressure reducing holes 15 are separately formed along the external circumference of the tube 14, and the pressure holes 15 reduce pressure generated due to the centrifugal force. In addition, an injection groove 18 is formed in the hydrogel column 17, and the pressure reducing holes 15 are formed at a side of the injection groove 18. Accordingly, nucleic acid in the injection groove 18 can be emitted to the housing 12 through the pressure reducing grooves 15 so that the nucleic acid recovery efficiency can be further improved.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

The invention claimed is:

1. A nucleic acid extracting method comprising the step of:
    forming a hydrogel column inside a pipe-shaped tube having an outlet formed in a lower portion of the tube;

forming an injection groove in the center of the hydrogel column extending in the length direction of the tube in the hydrogel column for holding a cell lysate; and forming a plurality of pressure reducing holes that contact the hydrogel column at an external circumference of the tube, wherein the cell lysate is formed by breaking cells; filtering the nucleic acid through the hydrogel column and extracting the nucleic acid passed through the hydrogel column externally.

2. The nucleic acid extracting method of claim 1, wherein the hydrogel column is formed of an agarose gel.

3. The nucleic acid extracting method of claim 2, wherein the agarose gel includes 1% to 2% agarose.

4. The nucleic acid extracting method of claim 2, wherein the agarose gel includes 0.5% to 5% agarose.

5. The nucleic acid extracting method of claim 2, wherein the forming of the hydrogel column comprises dissolving agarose by adding the agarose into distilled water and heating the mixture.

6. The nucleic acid extracting method of claim 5, wherein the forming of the hydrogel column further comprises injecting the mixture of the distilled water and the agarose into a tube and hardening the mixture.

7. The nucleic acid extracting method of claim 1, wherein the forming of the cell lysate comprises adding a lysis buffer and a proteinase K into a cell.

8. The nucleic acid extracting method of claim 1, wherein the forming of the cell lysate further comprises adding an RNase into a cell.

9. The nucleic acid extracting method of claim 1, wherein the hydrogel column is formed as a rotating body shape.

10. The nucleic acid extracting method of claim 1, wherein the filtering of the nucleic acid filters the nucleic acid by using a centrifugal separation method.

11. The nucleic acid extracting method of claim 10, wherein the centrifugal separation method comprises rotating the hydrogel column in a speed range of 1000 rpm to 3000 rpm.

12. The nucleic acid extracting method of claim 1, wherein the filtering of the nucleic acid is performed by using pressure.

13. The nucleic acid extracting method of claim 1, wherein the cell is a biological sample.

14. The nucleic acid extracting method of claim 1, wherein the cell is selected from the group consisting of an animal sample, a plant sample, and a microscopic organism sample.

15. The nucleic acid extracting method of claim 1, wherein the nucleic acid is DNA.

16. The nucleic acid extracting method of claim 1, comprising using the extracted nucleic acid in a genome test.

17. The nucleic acid extracting method of claim 1, comprising using the extracted nucleic acid in a DNA chip test.

18. The nucleic acid extracting method of claim 1, comprising using the extracted nucleic acid in point-of-care testing.

19. The nucleic acid extracting method of claim 1, wherein the nucleic acid extracting method is applied for testing a human-derived cell selected from the group consisting of a blood, a blood serum, a blood plasma, a bone marrow, an urine, a feces, a sputum, a cell aspirate, a tissue, and the tissue-derived material.

* * * * *